(12) United States Patent
Xiu et al.

(10) Patent No.: US 9,204,846 B2
(45) Date of Patent: Dec. 8, 2015

(54) LED LAMP AND AN X-RAY DEVICE AND A COLLIMATOR COMPRISING THE LED LAMP

(71) Applicant: GE MEDICAL SYSTEMS GLOBAL TECHNOLOGY COMPANY, LLC, Waukesha, WI (US)

(72) Inventors: Wenwen Xiu, Beijing (CN); Wen Gao, Beijing (CN); Yuqing Li, Beijing (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 280 days.

(21) Appl. No.: 13/870,243

(22) Filed: Apr. 25, 2013

(65) Prior Publication Data

US 2013/0287180 A1 Oct. 31, 2013

(30) Foreign Application Priority Data

Apr. 28, 2012 (CN) .......................... 2012 1 0142496

(51) Int. Cl.
| | |
|---|---|
| *A61B 6/08* | (2006.01) |
| *F21K 99/00* | (2010.01) |
| *F21V 19/00* | (2006.01) |
| *F21V 5/04* | (2006.01) |
| *F21V 29/00* | (2015.01) |
| *F21V 21/14* | (2006.01) |
| *F21Y 101/02* | (2006.01) |
| *F21V 29/77* | (2015.01) |
| *F21V 29/78* | (2015.01) |

(52) U.S. Cl.
CPC ... *A61B 6/08* (2013.01); *F21K 9/30* (2013.01); *F21K 9/50* (2013.01); *F21V 5/04* (2013.01); *F21V 19/001* (2013.01); *F21V 29/004* (2013.01); *F21V 21/14* (2013.01); *F21V 29/2212* (2013.01); *F21V 29/773* (2015.01); *F21V 29/78* (2015.01); *F21Y 2101/02* (2013.01)

(58) Field of Classification Search
CPC .............. F21V 19/001; F21V 19/0055; F21V 29/2212; F21V 5/04; F21V 21/14; F21V 29/004; F21V 29/773; A61B 6/08; F21K 9/30; F21K 9/50
USPC .......... 378/145, 147, 204–206; 362/218, 264, 362/294, 373, 545, 547, 612, 800
See application file for complete search history.

(56) References Cited

U.S. PATENT DOCUMENTS

| | | | | |
|---|---|---|---|---|
| 6,036,362 | A * | 3/2000 | Schmitt .......................... | 378/206 |
| 6,305,842 | B1 * | 10/2001 | Kunert .......................... | 378/206 |
| 6,653,661 | B2 * | 11/2003 | Okazaki .................. | H01L 33/54 257/100 |
| 6,874,910 | B2 * | 4/2005 | Sugimoto ........... | H01L 25/0753 257/98 |
| 7,050,544 | B2 * | 5/2006 | Karlsson et al. .............. | 378/158 |
| 7,098,485 | B2 * | 8/2006 | Isokawa .................. | H01L 33/54 257/98 |

(Continued)

FOREIGN PATENT DOCUMENTS

CN WO 2011/094901 A1 * 8/2011 .............. F21V 23/00

*Primary Examiner* — Allen C. Ho
(74) *Attorney, Agent, or Firm* — GE Global Patent Operation; Marc A. Vivenzio

(57) ABSTRACT

An embodiment of the present invention discloses a LED lamp as well as a X-Ray device and a collimator comprising the LED lamp. The LED lamp comprises a single LED chip serving as the light-emitting member of the LED lamp for emitting light beams; and a convex lens mounted in front of the LED chip for converging the light beams emitted from the LED chip. Embodiments of the invention can save power, reduce cost, and facilitate mass production and assembly.

15 Claims, 3 Drawing Sheets

(56) References Cited

U.S. PATENT DOCUMENTS

| | | | |
|---|---|---|---|
| 7,380,986 B2 * | 6/2008 | Brandstatter et al. | 378/206 |
| 7,499,288 B2 * | 3/2009 | Tanaka | H01L 33/486 361/760 |
| 7,728,342 B2 * | 6/2010 | Yoshida | B29C 45/14655 257/100 |
| 7,767,475 B2 * | 8/2010 | Masui | H01L 33/507 257/98 |
| 7,869,675 B2 * | 1/2011 | Urano | H01L 33/52 349/113 |
| 7,878,695 B2 * | 2/2011 | Ishida | F21S 48/1154 362/296.01 |
| 7,878,710 B2 * | 2/2011 | Kashiwagi et al. | 378/206 |
| 8,278,678 B2 * | 10/2012 | Masui | H01L 33/52 257/100 |
| 8,467,495 B2 * | 6/2013 | Okada et al. | 378/41 |
| 8,613,530 B2 * | 12/2013 | Allen et al. | 362/308 |
| 8,622,589 B2 * | 1/2014 | Chen et al. | 362/373 |
| 8,907,361 B2 * | 12/2014 | Kim | 257/98 |
| 9,127,824 B2 * | 9/2015 | Zhang | F21S 8/02 |
| 2004/0131157 A1 | 7/2004 | Stevanovic et al. | |
| 2013/0010470 A1 * | 1/2013 | Min | F21V 7/0025 362/238 |

* cited by examiner

A

B

LED LAMP AND AN X-RAY DEVICE AND A COLLIMATOR COMPRISING THE LED LAMP

BACKGROUND OF THE INVENTION

Embodiments of the present invention relate in general to the field of X-Ray detection, and more specifically to a collimator of X-Ray device, wherein the collimator uses a LED lamp to indicate the X-Ray field.

The current classical collimator is designed to have a halogen lamp with reflection to produce a light field to indicate an X-Ray field. This design has at least the following disadvantages.

First, the halogen lamp has a short life. Under normal usage, with the best halogen lamp for the collimator of a X-Ray device, such as a Mammo (mammography) radiography device, it will burn out at 3 years at most, which requires field engineers to periodically replace the lamp. This brings in service cost and decreases customer satisfaction.

Second, the halogen lamp is quite hot. To produce enough brightness, high energy is needed, and heat is generated with high power. This makes the lamp hot, and the temperature is about 150° C. The heat also brings in air flow. The air flow brings in dust which makes the collimator dirty and the light brightness decreases as the dust increases.

Third, the halogen lamp is expensive. A Halogen lamp is mainly structured by a halogen bulb, DC module and mechanical parts which increases maintenance/repair and component replacement costs.

Fourth, the halogen lamp with reflection cannot produce an X-Ray field with high brightness uniformity. The reflection part, shaped similar to a round cup with a hole at the cup bottom, cannot cover complete half ball around the halogen lamp. This makes a black zone in the center of the light field. To make up this non-uniformity, a diffuser is added before the lamp.

Lastly, the halogen bulb in the lamp product consistency is poor. The filament position sometimes deviates from the center, and this is a product defect distinct of the halogen lamp that cannot change. This character brings a high material defect rate to the production team.

BRIEF DESCRIPTION OF THE INVENTION

Embodiments of the present invention provide a LED lamp. The LED lamp comprises a single LED chip serving as a light-emitting member of the LED lamp configured to emit light beams. The LED lamp further comprises a convex lens, mounted in front of the single LED chip configured to converge the light beams emitted from the single LED chip.

Other embodiments of the invention provide a collimator for an X-Ray device. The collimator comprises an LED lamp comprising a single LED chip serving as a light-emitting member of the LED lamp configured to emit light beams, and a convex lens mounted in front of the single LED chip and configured to converge the light beams emitted from the single LED chip. The LED lamp illuminates an X-Ray field of the X-Ray device to indicate the X-Ray field.

Other embodiments of the invention provide an X-Ray device comprising a collimator comprising an LED lamp. The LED lamp comprises a single LED chip serving as a light-emitting member of the LED lamp configured to emit light beams, and a convex lens mounted in front of the single LED chip to converge the light beams emitted from the single LED chip. The LED lamp illuminates an X-Ray field of X-Ray device to indicate the X-Ray field.

BRIEF DESCRIPTION OF THE DRAWINGS

Features of embodiments of the present invention will become evident from the following description when taken in conjunction with the following drawings, wherein.

DETAILED DESCRIPTION OF THE INVENTION

Embodiments of the present invention are directed to an improved LED lamp. In some embodiments the LED lamp is applied to an X-Ray device such as, for example, a Mammo X-Ray device (e.g. mammography x-ray machine). And in some such embodiments the LED lamp is applied to a collimator of an X-Ray device.

Figure 1:
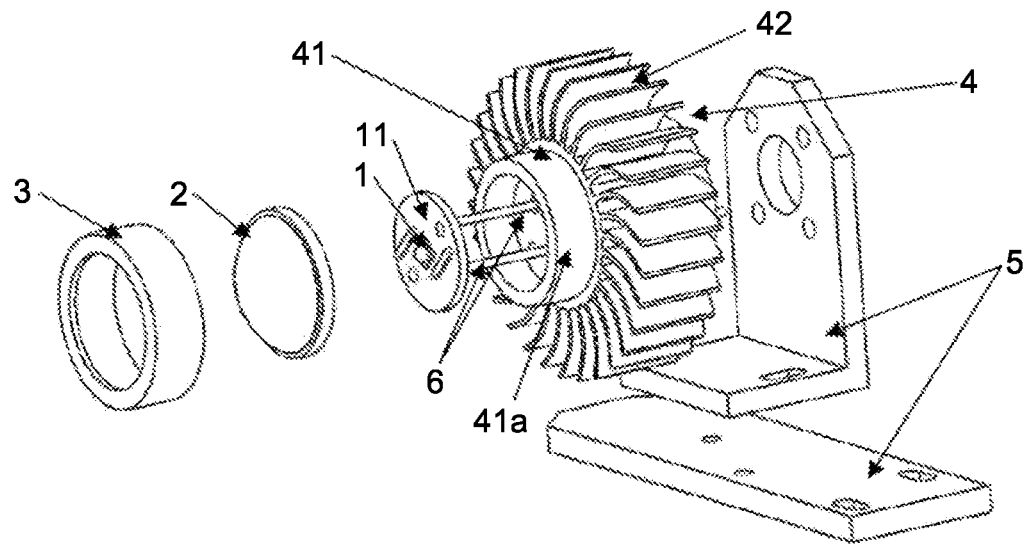
FIG. 1 is an exploded view of the LED lamp according to an embodiment of the invention.

FIG. 1 is an exploded view of the LED lamp according to an embodiment of this invention. As shown in FIG. 1, the LED lamp comprises a single LED chip 1 serving as the light-emitting member of the LED lamp for emitting light beams and a convex lens 2 is mounted in front of the LED chip 1 (see FIG. 2) for converging the light beams emitted from the LED chip 1.

In the past, in order to achieve enough illumination, many LED chips were needed to form a matrix as the light-emitting part, but the focus of such matrix was too large as compared to an X-Ray tube focus, so it could not be used in the collimator of an X-Ray device. By combining the LED chip matrix with a concave lens, the light beam is larger than the bare LED light beam without the use of a lens, thereby obtaining better edge contrast.

Figure 3:
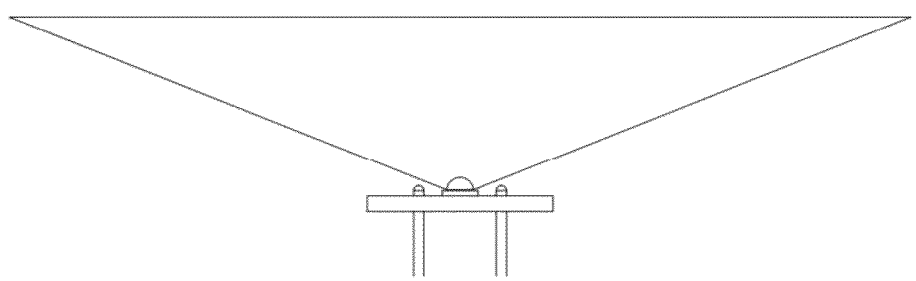
FIG. 3A-B are schematic diagrams respectively showing the LED light beams without the action of a convex lens and with the action of a convex lens according to an embodiment of the invention.
Figure 3:
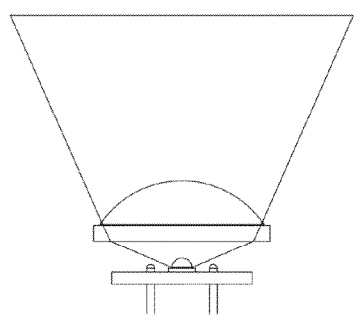

The design of the LED lamp according to an embodiment of the present invention is different from the conventional design. In this design, a single small-sized LED chip is used and is combined with a convex lens, thus having a brighter light beam and a smaller angle of divergence as compared with the bare LED light beam without the use of a lens (which can be seen from FIG. 3A-B).

Figure 2:
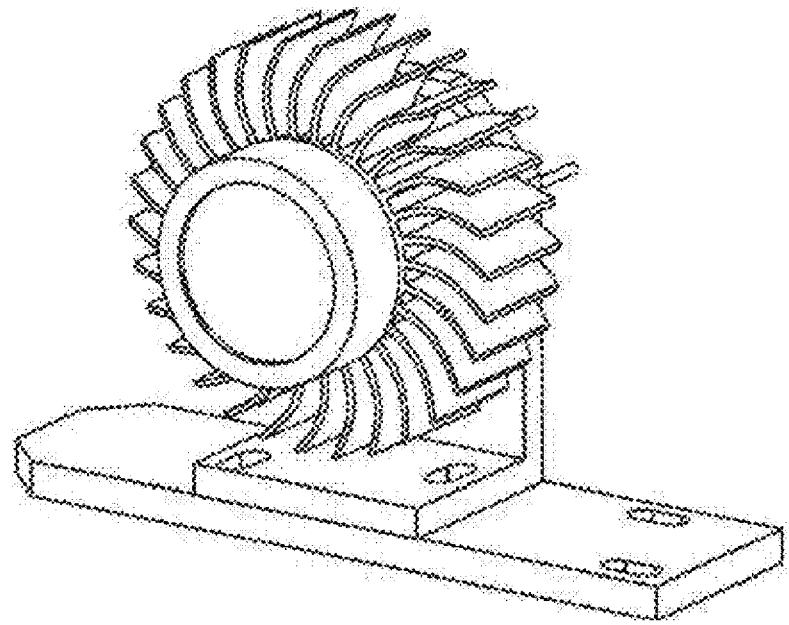
FIG. 2 is a schematic diagram of the LED lamp assembled and mounted on the mounting bracket according to an embodiment of the invention.

In an embodiment illustrated in FIGS. 1 and 2, besides the LED chip 1 and the convex lens 2, the LED lamp further comprises a lens cover 3, which contains the convex lens 2, for protecting the convex lens 2 and preventing the convex lens 2 from being blemished. The face of the lens cover 3 opposite to the convex lens 2 is optically transparent, so the LED light beam passing through the convex lens 2 can transmit freely through the lens cover 3. The LED lamp in this embodiment further comprises a heat radiator 4 for cooling off the LED lamp. FIGS. 1 and 2 further show a mounting bracket 5 for fixing the above parts of the LED lamp. In general, the mounting bracket 5 is adjustable.

Figure 4A:
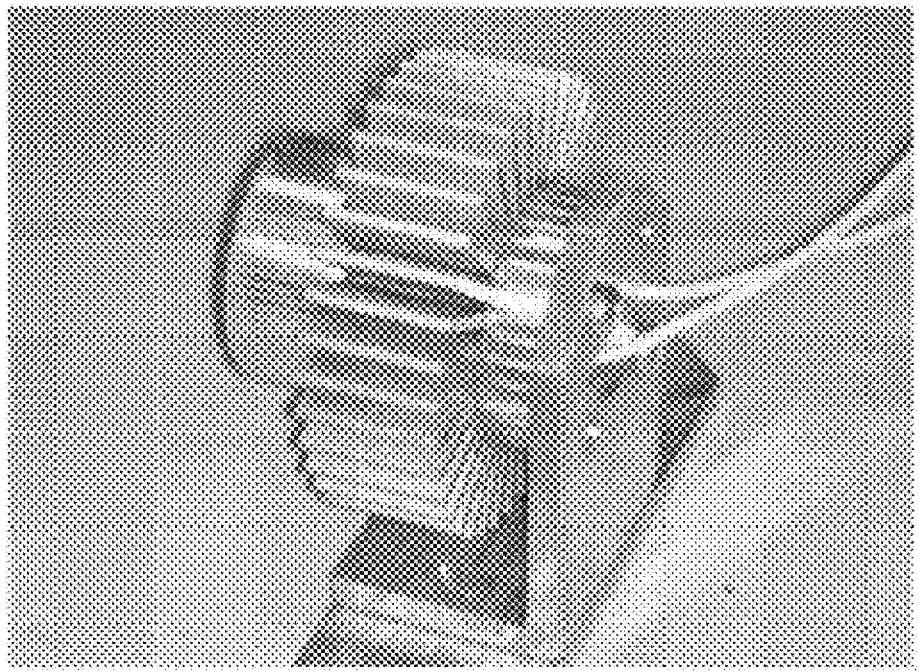
FIG. 4A-B are schematic diagrams respectively showing the heat radiator of the LED lamp in the prior art and the heat radiator of the LED lamp according to an embodiment of the invention.
Figure 4B:
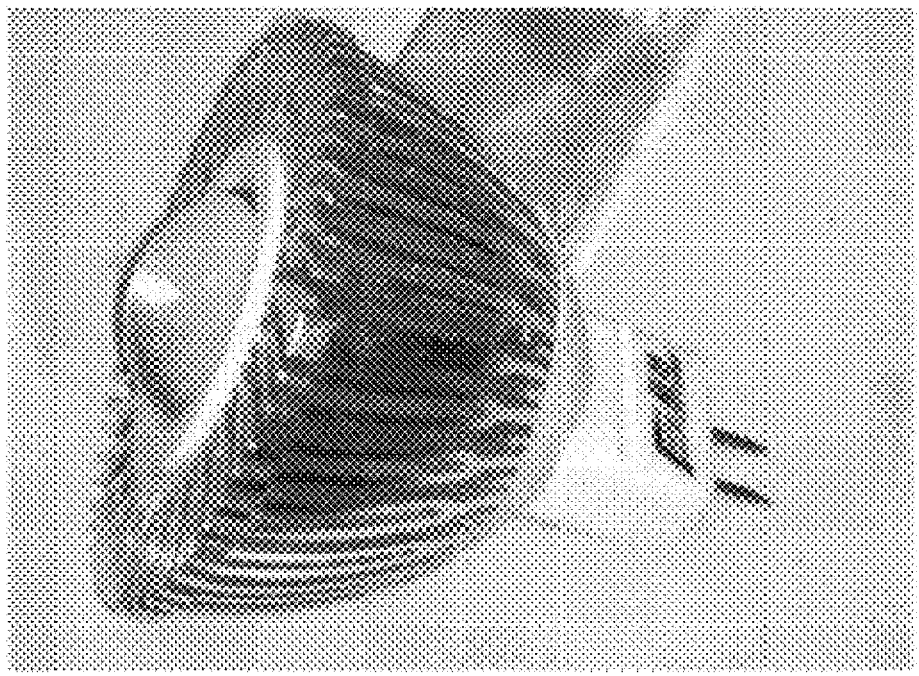

FIGS. 4A-B respectively show the heat radiator of the LED lamp according to an embodiment of the present invention and the heat radiator of the LED lamp in the prior art It can be seen from FIGS. 4A-B that the conventional LED lamp has a heat radiator with a cup figure. This cup-like heat radiator will interfere with other parts in the collimator and occupy a large space therein. The heat radiator 4 according to an embodiment of the present invention comprises a cylindrical substrate 41 and a plurality of laminas 42 mounted in a. radial pattern on the surface of the cylindrical substrate 41. Thanks to this cylindrical heat radiator design, this LED lamp component will not affect other parts in the collimator.

In the embodiments shown by FIGS. 1 and 2, the LED chip 1 of the LED lamp is mounted on a circular base 11, wherein a cable 6 in FIG. 1 is the power line of the LED chip 1. It can be seen from the chart of the assembled LED lamp in FIG. 2 that the circular base 11 attached with an LED chip 1 is contained in the cylindrical substrate 41 of the heat radiator 4. In an embodiment, the circular base 11 attached with an LED chip 1 is mounted to the bottom of the cylindrical substrate 41 by screw or any other suitable fastener mechanical or otherwise as recognized by those skilled in the art. The circular base 11 may be mounted in any of multiple positions of the cylindrical substrate 41 in other mounting manners. In an embodiment, the cylindrical inner wall of the lens cover 3 containing the convex lens 2 is chiseled with screw threads, and the cylindrical substrate 41 of the heat radiator 4 has a head end 41a without being covered by laminas 42, the outer wail of the head end 41 a is also chiseled with screw threads corresponding to the screw threads on the lens cover 3. The lens cover 3 containing the convex lens 2 can be sheathed on the head end 41 a of the cylindrical substrate 41 of the heat radiator 4 in a threaded mounting manner. The head end 41a corresponds to the head end opposite to the LED chip 1, to ensure that after the mounting, the light beam emitted from the LED chip 1 will be converged by the convex lens 2. By properly designing the distance between the LED chip 1 and the convex lens 2, and making the mounting maintain this distance, an LED light beam can comprise a fine edge contrast, enough field brightness, and uniformity.

In an embodiment of the present invention, the LED lamp uses the small focus and high power of the single LED chip 1, so the structure is simple. The size of the LED lamp is smaller than a halogen lamp and is easy to design to fit multiple new and former product positions, so it has flexibility and perfect backward compatibility. The current halogen lamp assembly used in the collimator has a dimension of about 92 mm×about 60 mm×about 60 mm (Long×Widtht×Height). This novel LED design has dimension of about 40 mm×about 46 mm×about 58 mm (Long×Width×Height).

The LED lamp according to the embodiments of this invention has one or more of the following advantages, particularly in comparison to prior art halogen bulb/lamp configurations.

First, the LED lamp according to the embodiments of this invention has a higher energy efficiency and generates less heat. The lens of the LED Lamp will not be quite hot as the power needed by it will be approximately equal to or less than 5 W. From a power perspective, it is $\frac{1}{10}$ of that of the halogen lamp, and most of the power in a LED lamp will be transferred into light, not heat, so the heat generated is little. The air flow caused by this heat will thus be much decreased.

Second, the LED lamp according to the embodiments of this invention has a longer service life. In a normal case, the LED chip 1 has a burning life of 20000 to 30000 hours. Using the LED lamp in the collimator of an X-Ray device for ten years is approximately equivalent to 10000 hours burning time. So if a LED lamp is used in a collimator, we would not need to replace the LED lamp because of a life issue, thus reducing the cost for on-site replacements.

Third, the LED lamp according to the embodiments of this invention provides a lower cost alternative. The LED lamp of this invention is mainly structured by the LED chip 1 and the convex lens 2. The ICV of this part is about $25. It can he seen that, as compared to a halogen lamp configuration, using the LED lamp of this invention saves, at the time of this application filing, more than $100 USD for each application.

Fourth, the LED lamp according to one embodiment of this invention does not require a heat radiator 4. The burning part of a LED lamp is the LED chip 1. In an embodiment of the present invention, the chip size is about 2 mm×2 mm, and it is a point of focus. So the LED lamp of an embodiment of the present invention will have high uniformity. A heat radiator 4 will not be needed.

Fifth, the LED lamp according to the embodiments of this invention has a higher product consistency. Said LED lamp has very high product consistency. The focal position of this lamp can be controlled by machining and electrical chip jointing. So, for mass production, the failure rate of producing the LED lamp is low, and production operators do not need to take a lot of adjustment for this lamp, thus the quality is easy to be controlled.

Table 1 shows the test result of one LED lamp sample according to an embodiment of the present invention, wherein the distance from the bulb tube focus to the X light receiving surface is 660 mm, FOV (field of vision) is 300 mm×240 mm.

TABLE 1

Test Result of LED Lamp Sample According to an Embodiment of the Present Invention.

| Function item | Production requirement | Test data |
| --- | --- | --- |
| Brightness | ≥300 lux | 349.5 lux |
| Uniformity | ≥75% | 91.70% |
| Edge Contrast | ≥4.5 | 5.53 |
| Misalignment to X-Ray field | ≤5 mm | 4 mm |

The LED lamp of an embodiment of the present invention is suitable for an X-Ray device. In an embodiment of the present invention, the LED lamp can be used in the collimator of a Mammo X-Ray device, so that the LED lamp can be used to illuminate the X-Ray field of the X-Ray device to indicate the X-Ray field. It should be understood that the LED lamp of an embodiment of the present invention is not limited to this application.

An embodiment of the present invention provides a LED lamp. The LED lamp comprises a heat radiator 4 to cool the LED lamp.

According to an embodiment of this invention, the LED lamp further comprises a lens cover 3 to contain the convex lens 2.

According to an embodiment of this invention, the LED lamp further comprises a mounting bracket 5 for fixing the LED chip 1 and the convex lens 2.

According to an embodiment of this invention, the heat radiator 4 comprises a cylindrical substrate 41 and a plurality of laminas 42 mounted in a radial pattern on the surface of the cylindrical substrate 41.

According to an embodiment of this invention, the cylindrical substrate 41 contains the LED chip 1.

According to an embodiment of this invention the LED chip 1 is mounted on a circular base 11, and the circular base 11 is contained in the cylindrical substrate 41.

According to an embodiment of this invention, the circular base 11 is mounted in the cylindrical substrate 41 by screws.

According to an embodiment of this invention, the lens cover 3 is mounted to the cylindrical substrate 41 in a manner of threaded mounting.

According an embodiment of the invention, a collimator used in an X-Ray device is provided. The collimator comprises a LED lamp, wherein the LED lamp illuminates an X-Ray field of the X-Ray device to indicate the X-Ray field.

According to another embodiment of the invention, an X-Ray device is provided. The X-Ray device comprises a collimator, and the collimator comprises a LED lamp, wherein the LED lamp illuminates an X-Ray field of the X-Ray device to indicate the X-Ray field.

According to an embodiment of this invention, the X-Ray device is a Mammo X-Ray device.

According to an embodiment, the LED lamp and an X-Ray device and/or a collimator comprising the LED lamp according to an embodiment of this invention can simplify structure, save space and reduce cost.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An LED lamp, comprising:
   a single LED chip serving as a light-emitting member of the LED lamp configured to emit light beams;
   a convex lens mounted in front of the single LED chip to converge the light beams emitted from the single LED chip;
   a lens cover containing the convex lens to transmit the light beams emitted from the single LED chip; and
   a heat radiator comprising a cylindrical substrate and a plurality of laminas mounted in a radial pattern on a surface of the cylindrical substrate, wherein the cylindrical substrate comprises a cylindrical head end which is not covered by the plurality of laminas.

2. The LED lamp according to claim 1, wherein the heat radiator cools the LED lamp.

3. The LED lamp according to claim 1, further comprising a mounting bracket, wherein the mounting bracket fixes the single LED chip and the convex lens.

4. The LED lamp according to claim 3, wherein the mounting bracket is adjustable.

5. The LED lamp according to claim 1, wherein the cylindrical substrate contains the single LED chip.

6. The LED lamp according to claim 1, further comprising a circular base, wherein the single LED chip is mounted on the circular base, wherein the circular base is contained in the cylindrical substrate.

7. The LED lamp according to claim 1, wherein the lens cover is mounted to the cylindrical substrate in a manner of threaded mounting.

8. The LED lamp according to claim 1, wherein the lens cover is mounted to the cylindrical substrate through the cylindrical head end.

9. The LED lamp according to claim 1, wherein the lens cover is cylindrical.

10. A collimator for an X-Ray device, comprising:
    an LED lamp comprising:
       a single LED chip serving as a light-emitting member of the LED lamp configured to emit light beams;
       a convex lens mounted in front of the single LED chip to converge the light beams emitted from the single LED chip;
       a lens cover containing the convex lens to transmit the light beams emitted from the single LED chip; and
       a heat radiator comprising a cylindrical substrate and a plurality of laminas mounted in a radial pattern on a surface of the cylindrical substrate, wherein the cylindrical substrate comprises a cylindrical head end which is not covered by the plurality of laminas,
       wherein the LED lamp illuminates an X-Ray field of the X-Ray device to indicate the X-Ray field.

11. The collimator according to claim 10, wherein the X-Ray device further comprises a Mammo X-Ray device.

12. The collimator according to claim 10, wherein the lens cover is cylindrical.

13. An X-Ray device comprising:
    a collimator comprising an LED lamp, the LED lamp comprising:
       a single LED chip serving as a light-emitting member of the LED lamp configured to emit light beams;
       a convex lens mounted in front of the single LED chip to converge the light beams emitted from the single LED chip;
       a lens cover containing the convex lens to transmit the light beams emitted from the single LED chip; and
       a heat radiator comprising a cylindrical substrate and a plurality of laminas mounted in a radial pattern on a surface of the cylindrical substrate, wherein the cylindrical substrate comprises a cylindrical head end which is not covered by the plurality of laminas,
       wherein the LED lamp illuminates an X-Ray field of the X-Ray device to indicate the X-Ray field.

14. The X-Ray device according to claim 13, further comprises a Mammo X-Ray device.

15. The X-Ray device according to claim 13, wherein the lens cover is cylindrical.

* * * * *

UNITED STATES PATENT AND TRADEMARK OFFICE
CERTIFICATE OF CORRECTION

PATENT NO. : 9,204,846 B2  
APPLICATION NO. : 13/870243  
DATED : December 8, 2015  
INVENTOR(S) : Xiu et al.

Page 1 of 1

It is certified that error appears in the above-identified patent and that said Letters Patent is hereby corrected as shown below:

In the Specification

In Column 2, Line 67, delete "art" and insert -- art. --, therefor.

In Column 3, Line 6, delete "in a." and insert -- in a --, therefor.

In Column 3, Line 27, delete "wail of the head end 41 a" and insert -- wall of the head end 41a --, therefor.

In Column 3, Line 30, delete "end 41 a" and insert -- end 41a --, therefor.

In Column 3, Line 46, delete "Widtht" and insert -- Width --, therefor.

In Column 4, Line 4, delete "can he" and insert -- can be --, therefor.

Signed and Sealed this
Sixteenth Day of August, 2016

Michelle K. Lee
*Director of the United States Patent and Trademark Office*